United States Patent [19]
Abidin et al.

[11] Patent Number: 5,222,951
[45] Date of Patent: Jun. 29, 1993

[54] GUARDED SKIN HOOK FOR SURGICAL USE

[75] Inventors: Michael R. Abidin; Steven P. Lehmbeck, both of Baltimore, Md.

[73] Assignee: Leonard Bloom, Towson, Md.; a part interest

[21] Appl. No.: 867,881

[22] Filed: Apr. 13, 1992

[51] Int. Cl.⁵ .................. A61B 17/00; A61B 19/00
[52] U.S. Cl. .................................. 606/1; 128/20; 30/162
[58] Field of Search .................. 128/20, 849-851; 604/159-162, 197, 198, 210; 606/1, 172, 167, 182, 190; 30/162

[56] References Cited

U.S. PATENT DOCUMENTS

| 292,917 | 2/1884 | Kaldenbach | 30/162 |
| 309,863 | 12/1884 | McGovern | 30/162 |
| 470,777 | 3/1892 | Billings | 30/162 |
| 734,590 | 7/1903 | Minnich | 30/162 |
| 806,333 | 12/1905 | Folden | 30/162 |
| 3,857,386 | 12/1974 | Ashbell | 128/20 |
| 4,616,635 | 10/1986 | Caspar et al. | 128/20 |
| 4,682,981 | 7/1987 | Suzuki et al. | 604/165 |
| 4,895,147 | 1/1990 | Bodicky et al. | 606/182 |

FOREIGN PATENT DOCUMENTS 3722899 1/1989 Fed. Rep. of Germany ...... 606/167

Primary Examiner—Stephen C. Pellegrino
Assistant Examiner—Glenn Dawson
Attorney, Agent, or Firm—Leonard Bloom

[57] ABSTRACT

A guarded skin hook for surgical use during a standard operational procedure. The guarded skin hook prevents accidental or inadvertent cuts or nicks during the procedure, thereby protecting the surgeon, nurse or other health care provider as the skin hook is passed from one to another in the operating room or similar environment. The guard has a "feel" which enables the surgeon or nurse to grasp the guarded skin hook without taking his or her eyes away from the patient.

22 Claims, 10 Drawing Sheets

O.R.

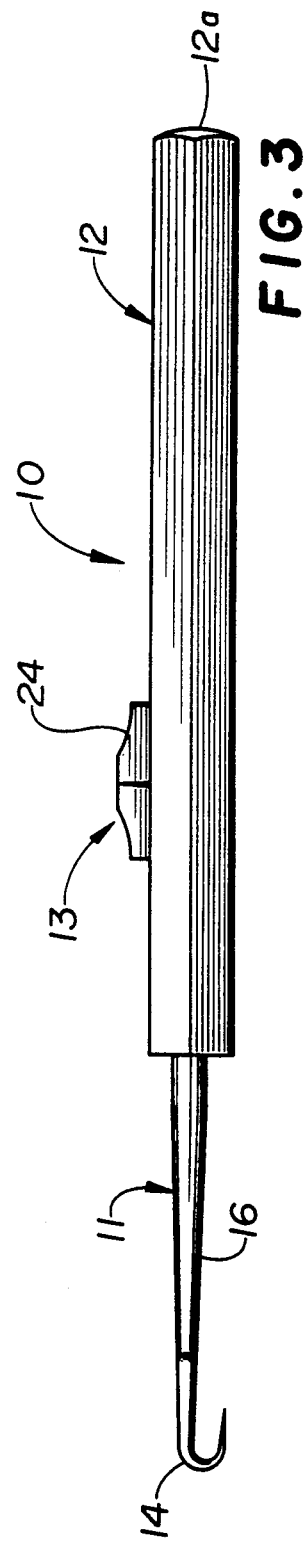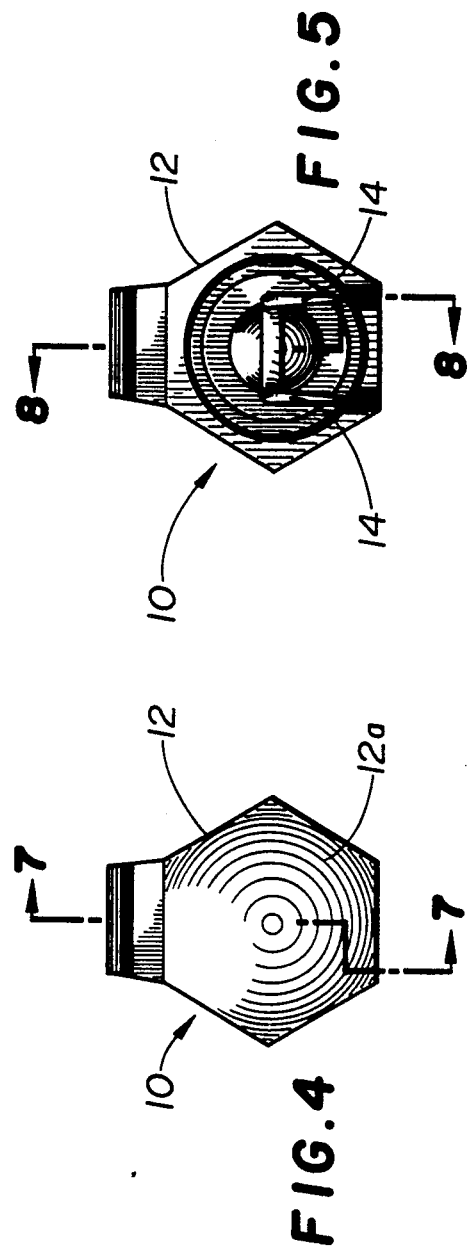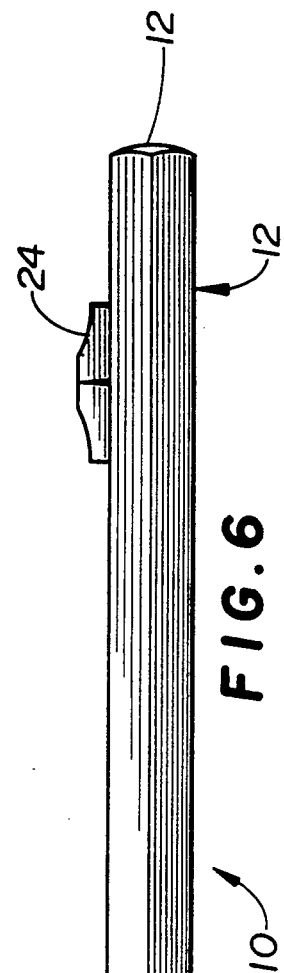

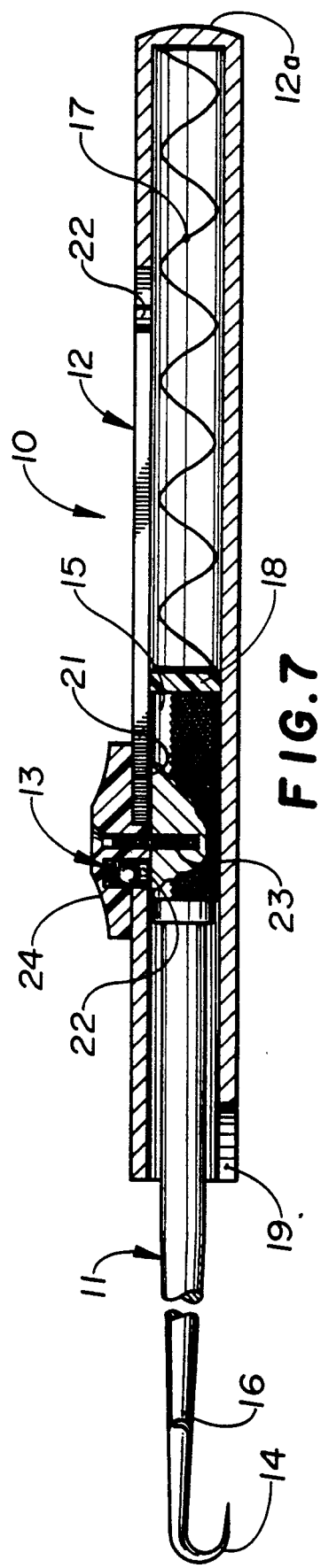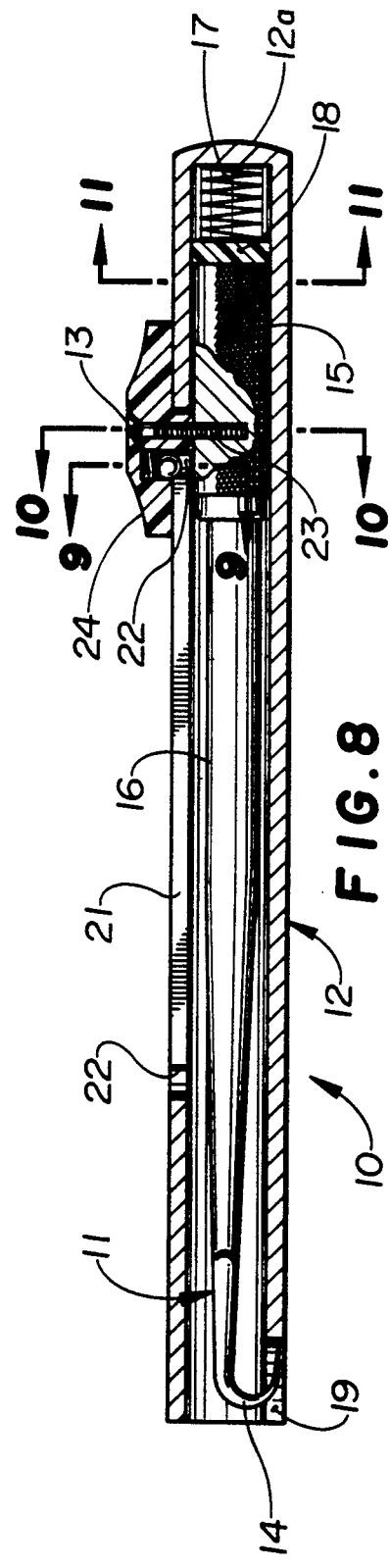

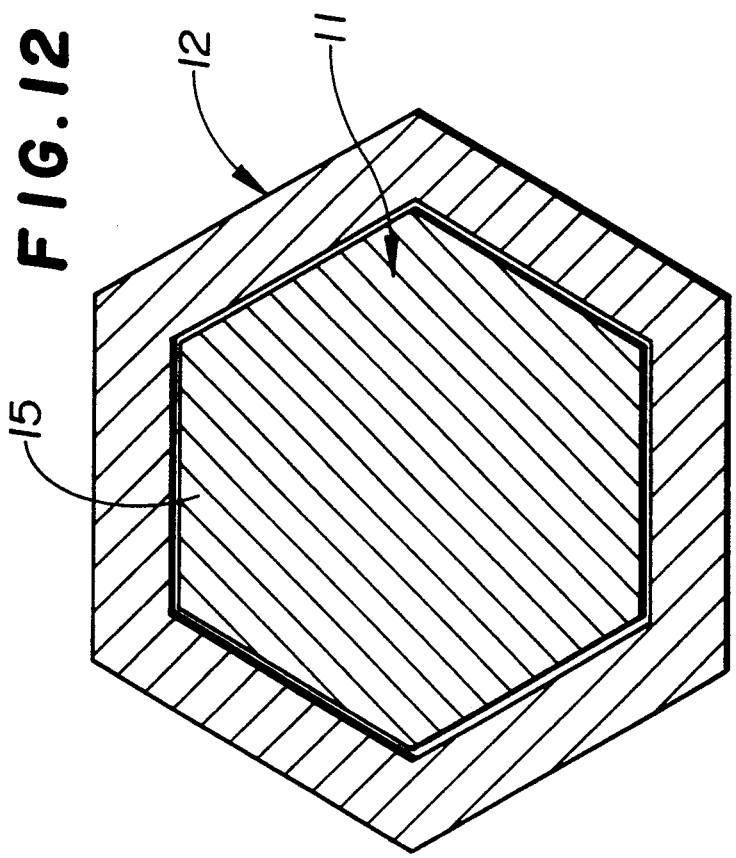
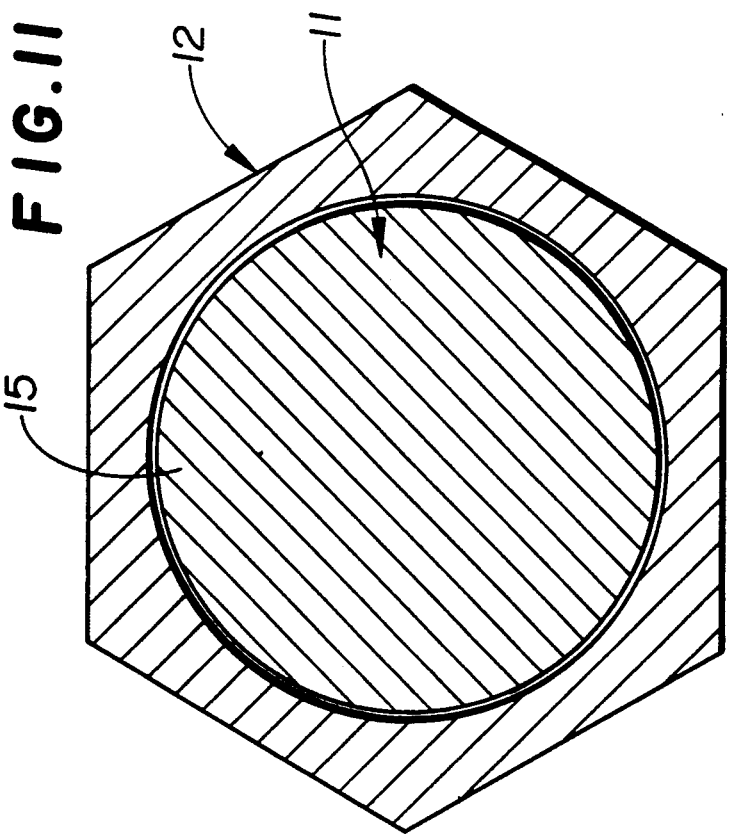

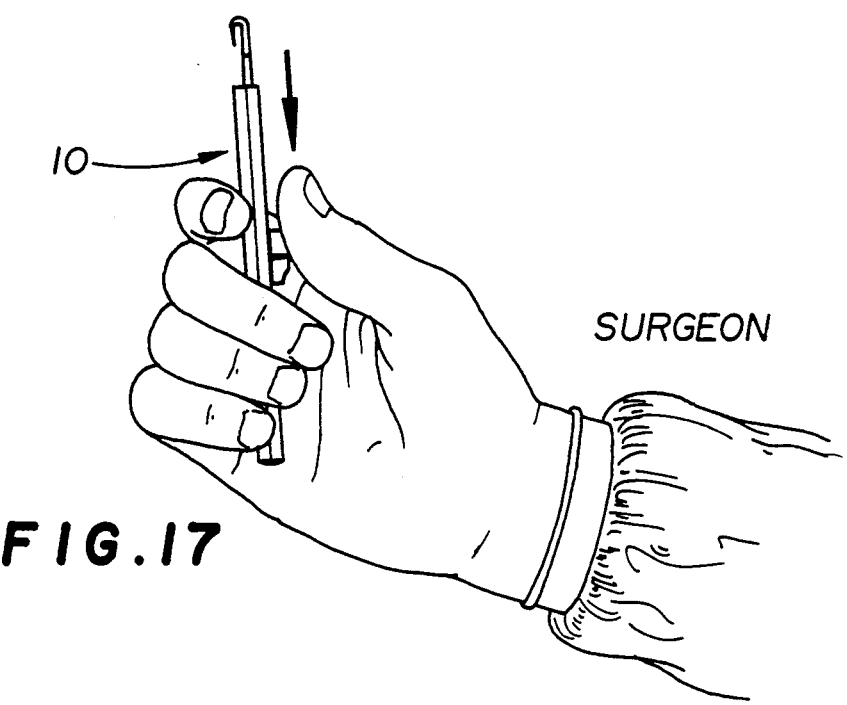
FIG. 17 SURGEON
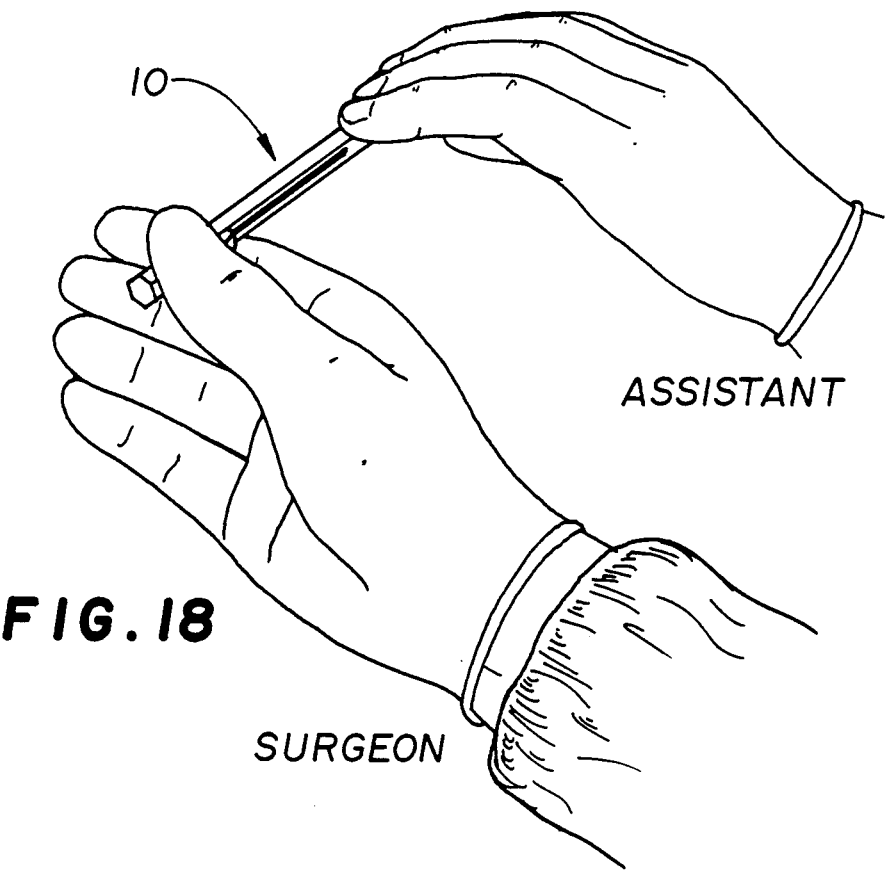
FIG. 18 ASSISTANT SURGEON

GUARDED SKIN HOOK FOR SURGICAL USE

FIELD OF THE INVENTION

The present invention relates to skin hooks for surgical use and, in particular, to a skin hook for surgical use that may be selectively retracted within, and thereafter extended from, a protective guard.

BACKGROUND OF THE INVENTION

Skin hooks are regularly used by surgeons and other allied health care professionals for pulling back and/or holding the skin along an incision during a surgical procedure. Conventional skin hooks are unguarded, that is to say, they have surgical prongs that are exposed or uncovered at all times. The only covers provided for such conventional skin hooks are "one-use" covers, such as frangible plastic sheaths, that are torn or otherwise removed from the skin hooks before their initial introduction to the doctor for usage during a routine surgical procedure.

During routine surgical procedures, the operating room assistant (which may be a nurse, another doctor or any other individual) has to "slap" the unguarded skin hook into the surgeon's hand. This must be done so that the surgeon can "feel" the skin hook's orientation and automatically grip the handle of the unguarded skin hook without taking his or her eyes off of the patient. Unfortunately, in doing so, the assistant is left highly exposed to the uncovered prongs of conventional skin hooks. Such exposure can, and often does, result in the nurse or assistant being pricked or otherwise cut by the prongs.

A surgeon is similarly unable to take his or her eyes off of the patient when handing the skin hook back to the nurse or other assistant. Thus, the surgeon is often unable to properly orient the uncovered prongs thereof. Once again, the assistant is often required to take a conventional unguarded skin hook from the doctor by gripping either the exposed surgical prongs thereof or a part of the skin hook that is in close proximity to the exposed prongs. As a result, the nurse or assistant is often pricked and or otherwise cut by the exposed prongs.

In both of the above cases, as well as when a conventional skin hook is left unattended in the surgical field, it is not uncommon for the surgeon's assistant, and sometimes even the surgeon, to be stuck by the exposed prongs of conventional unguarded skin hooks. Such cuts, in addition to being extremely uncomfortable, can lead to the spreading of infection and disease. Concern over this situation has become especially acute since the appearance of the HIV virus. Indeed, such punctures have already been blamed, by some health care providers, for cases of HIV infection leading to the deadly AIDS disease. Consequently, some health care providers have gone so far as to stop performing surgical operations altogether, rather than risk the chances of inadvertently contracting the deadly HIV virus from an infected patient.

Similar concerns are presented relative to the Hepatitis B virus (also referred to herein as "HBV").

The risks associated with a puncture from conventional unguarded skin hooks during an operating room procedure are greater than those associated with needle sticks; but even there, the problem is becoming alarming. In a study made by the Needle Stick Surveillance Group of the C.D.C. (Centers for Disease Control) out of 3,978 known punctures from patients known to be HIV positive, 13 health care workers got infected, or roughly 1 out of 300. Thus, from a single needle stick while treating an AIDS patient in an operating room or other environment, the chances are roughly 1 out of 300 that the surgeon, nurse or other individual health care provider will sero-convert and become HIV positive.

If a surgeon, nurse or assistant is stuck by a skin hook while conducting a surgical procedure in an operating room (rather than a needle stick) the risk is much greater. This is simply because, first, there is more blood involved in a surgical procedure and, secondly, the surface area of the wound is larger. In operating on an HIV positive patient, and even if the chances of becoming HIV positive from a puncture sustained from a skin hook are substantially the same as the needle sticks—roughly 1 out of 300—if the surgeon or nurse performs just one operating room procedure on an HIV-positive patient per day for 6 days a week, 50 weeks per year, then the chances of becoming HIV positive through an inadvertent puncture in an operating room procedure are virtually guaranteed.

This situation has become so pronounced that some leading surgeons, as well as nurses and other individual health care providers, have abandoned their respective practices.

While the use of protective gloves aid in reducing the chances of being cut during a surgical operation, the use of such gloves are by no means foolproof, and such cuts are still quite common. Even when two sets of gloves are utilized, full protection is not afforded to the health care provider, for many times the razor-sharp surgical prongs of the skin hook cut right through both sets of gloves. Also, utilizing two sets of gloves at the same time reduces the wearers finger dexterity, thereby presenting problems with performing the intended surgical procedure and tending to reduce the effectivity thereof.

To the best of our knowledge, there are no surgical skin hooks which are fitted or otherwise equipped with a protective guard or cover which may be movable relative to one another so as to be used to selectively guard or cover the surgical prongs of a skin hook during a surgical procedure in order to protect against inadvertent contact therewith which may result in cuts or punctures.

It is noted that, to be readily adaptable for use during a standard surgical procedure in a standard operating theater, it is preferred that a skin hook having a guard therefor have any and/or all of the following features:

(1) adaptability that permits the protective guard to be retracted from, and replaced in position over, the surgical prongs of the skin hook with the use of only one hand;

(2) means that permits the doctor (or other user of the skin hook) to be able to readily and tactily identify the mechanism or element which permits (releases and/or locks) the protective guard and the skin hook to be moved relative to one another, so that these elements can be placed in the selected position desired without the user thereof having to remove his or her eyes from the patient in order to visually observe the skin hook;

(3) the shape of the protective guard should substantially approximate the shape of the body of the skin hook by which the guard is carried, so that during use thereof, the user may utilize a grip that substantially approximates the grip that is normally utilized, thereby providing the user with a good and comfortable "feel" when performing the surgical operating procedure, and further so that rotation of the skin guard relative to the protective hook is prevented; and (4) the skin hook should provide an auditory sound means, whereby the user may be made aware that the protective guard and the skin hook have actually been locked into their selected positions relative to one another without the necessity of having to remove his or her eyes from the patient in order to visually observe the instrument.

Thus, it can be seen that there further remains a need for a surgical skin hook that has a protective guard which is readily adaptable for use during a standard surgical procedure in an operating theater by providing the skin hook with any and/or all of the aforementioned elements.

SUMMARY OF THE INVENTION

It is a primary object of the present invention to provide a guarded surgical skin hook which includes a protective guard for selectively covering and uncovering the prongs thereof during a surgical procedure, so as to selectively afford protection against inadvertent contact therewith, or to be exposed for use thereof.

It is another primary object of the present invention to provide such a guarded surgical skin hook which has a protective guard that is readily adaptable for use during a surgical procedure in a standard operating theater.

So as to be adaptable for use during a standard surgical procedure, it is an object of the present invention to provide such a guarded surgical skin hook that has a protective guard which is movable relative to the skin hook, so that the protective guard can be retracted from, and replaced in position over, the surgical prongs of the skin hook with the use of only one hand.

So as to be further adaptable for use during a standard surgical procedure, it is yet another object of the present invention to provide such a guarded skin hook which permits the surgeon (or other user thereof) to be able to readily and tactily identify the mechanism or element which locks and/or releases the protective guard and the skin hook relative to one another, so that these elements can be placed in the selected position desired without the necessity of the user having to remove his or her eyes from the patient in order to visually observe the skin hook.

So as to be still further adaptable for use during a standard surgical procedure, it is yet another object of the present invention to provide such a guarded skin hook wherein the shape of the protective guard of the skin hook substantially approximates the shape of the body of the skin hook by which it is carried, so that during use thereof, the user may utilize a grip that substantially approximates the grip that is normally utilized, thereby providing the user with a good and comfortable "feel" when performing the surgical operating procedure, and further such that relative rotation of the skin hook relative to the protective guard is prevented.

So as to be still yet adaptable for use during a standard surgical procedure, it is yet another object of the present invention to provide a guarded skin hook that includes an auditory sound means, whereby the user may be made aware that the protective guard and the skin hook have actually been locked into their selected positions relative to one another without the necessity of having to remove his or her eyes from the patient in order to visually observe the skin hook.

In accordance with the teachings of the present invention, a guarded skin hook for surgical use is disclosed. This guarded skin hook includes a main body portion having a forward section, from which the skin hook extends, and a rearward end. A guard in the form of a guard sleeve is provided for slidably receiving therein the skin hook including the main body portion thereof. Means is provided for slidably mounting the skin hook within the guard sleeve for limited longitudinal sliding movement of the skin hook relative to the body between a first, extended position and a second, retracted position. In the first position, the skin hook is extended from the guard sleeve, so as to be exposed for usage thereof. In the second position, the skin hook is retracted inside the guard sleeve so as to be covered by the guard sleeve for affording protection against accidental contact with the skin hook when not in usage. In this fashion, surgeons, nurses and the like in an operating room may pass the skin hook from between the first extended and second retracted positions with a one-hand movement without taking his or her eyes away from the patient. Such an arrangement prevents cuts or nicks normally encountered in the usage and passing of skin hooks between surgeons, nurses and the like during an operating procedure. As a result, the risk of surgeons, nurses and the like inadvertently acquiring an infectious disease, such as HIV or HBV in an operating room or similar medical environment, is substantially reduced.

In a preferred embodiment, the guarded skin hook further includes a release means for selectively unlocking the skin hook and the protective guard, so that the guard is released for the sliding movement thereof. The release means is formed so as to extend outwardly from the guard sleeve. In this manner, the release means may be readily and tactily identified and utilized by a user without the necessity of the user having to visually observe the instrument. Further in this manner, the release means is operable with one hand, so that the guard sleeve and the skin hook may be unlocked from one another, released and longitudinally slidingly moved between the extended and retracted positions thereof with the use of only one hand.

In another preferred embodiment, the skin hook still further includes a locking means. This locking means actively and solidly fixes (that is, positively locks) the skin hook and the protective guard in position relative to one another, so that they will not be accidentally dislodged or moved as a result of the ordinary pressure that is, by necessity, exerted thereon by the user while gripping the skin hook during the use thereof. Preferably, the locking means automatically locks the skin hook and the protective guard into their respective positions relative to one another when the guard of the skin hook is in its extended or retracted positions. In this manner, the locking means further facilitates the ability of the guarded skin hook of the present invention to be utilized with the use of only one hand.

In yet another preferred embodiment, the guard sleeve is formed so as to substantially approximate the shape of the body of the skin hook. In this manner, during use of the guarded skin hook, the user may utilize a grip that substantially approximates the grip that is normally utilized so as to provide the user with a comfortable "feel" during use of the skin hook. Further in this manner, relative rotation of the skin hook within the protective guard is prevented.

In another preferred embodiment, the guarded skin hook further includes a means that emits an auditory signal or "click" at the moment when the protective guard sleeve and the skin hook are locked into their selected positions relative to one another. In this manner, the user may be made aware that the protective guard and the skin hook have actually been locked into their selected positions relative to one another without the necessity of having to visually observe the skin hook.

Viewed in another aspect, the present invention provides a guarded skin hook for use in surgical procedures. The guarded skin hook includes a first member having a forward portion provided with at least one hook formed thereon. A second member telescopically receives the first member, and means are provided for mounting the first and second members for limited relative longitudinal sliding movement therebetween. As a result, the guarded skin hook has a first operational position in which the first member extends outwardly of the second member, such that the hook o the first member is exposed; and the guarded skin hook further has a second guarded position in which the first member is retracted within the second member, such that the hook is not exposed, thereby protecting against accidental or inadvertent nicks as the guarded skin hook is passed from an assistant to a surgeon, and vice versa, during a procedure in an operating room.

These and other objects of the present invention will become readily from a reading of the following description of the present invention, taken in conjunction with the enclosed drawings.

BRIEF DESCRIPTION OF THE DRAWINGS

FIG. 3 is a side elevation of the preferred embodiment of the guarded skin hook of the present invention with the skin hook thereof in a first extended position, whereby the surgical prongs thereof are exposed for the use thereof.

FIG. 4 is a rear end view of the guarded skin hook of FIG. 3, drawn to an enlarged scale.

FIG. 5 is a front view, drawn to an enlarged scale, of the preferred embodiment of the guarded skin hook with the skin hook thereof in a second retracted position.

FIG. 6 is a side elevation of the guarded skin hook of FIG. 3, with the ski hook thereof in a second retracted position, whereby the surgical prongs thereof are covered, so that protection may be afforded to the surgeon and the assistant during an operating procedure.

FIG. 7 is a longitudinal section view taken along lines 7—7 of FIG. 4, the prongs being in their extended position.

FIG. 8 is a longitudinal section view taken along lines 8—8 of FIG. 5, the prongs being in their retracted position.

FIG. 11 is a cross-sectional view taken along lines 11—11 of FIG. 8.

FIG. 12 corresponds substantially to FIG. 11, but shows a modification thereto wherein the guard sleeve and the main body of the skin hook of the present invention are complementary-shaped, preferably hexagonal, so as to be keyed to one another.

FIGS. 15-18 illustrate the use of the guarded skin hook of FIGS. 3-13 and, in particular, the protection afforded to the health care providers in passing the guarded skin hook during an operating procedure.

FIG. 15 illustrates how the guard of the skin hook of the present invention protects the assistant's hands when the skin hook is passed from the assistant to the surgeon during an operating procedure.

FIG. 16 illustrates how the guarded skin hook is moved with one hand by the surgeon, so that the surgical prongs of the skin hook are exposed for permitting the normal use thereof.

FIG. 17 illustrates how the guarded skin hook is moved with one hand by the surgeon, so that the surgical prongs of the skin hook are covered.

FIG. 18 illustrates how the guard of the skin hook of the present invention protects the surgeon's hand when the skin hook is passed from the surgeon to the assistant during an operating procedure.

DESCRIPTION OF PREFERRED EMBODIMENT

Figure 1:
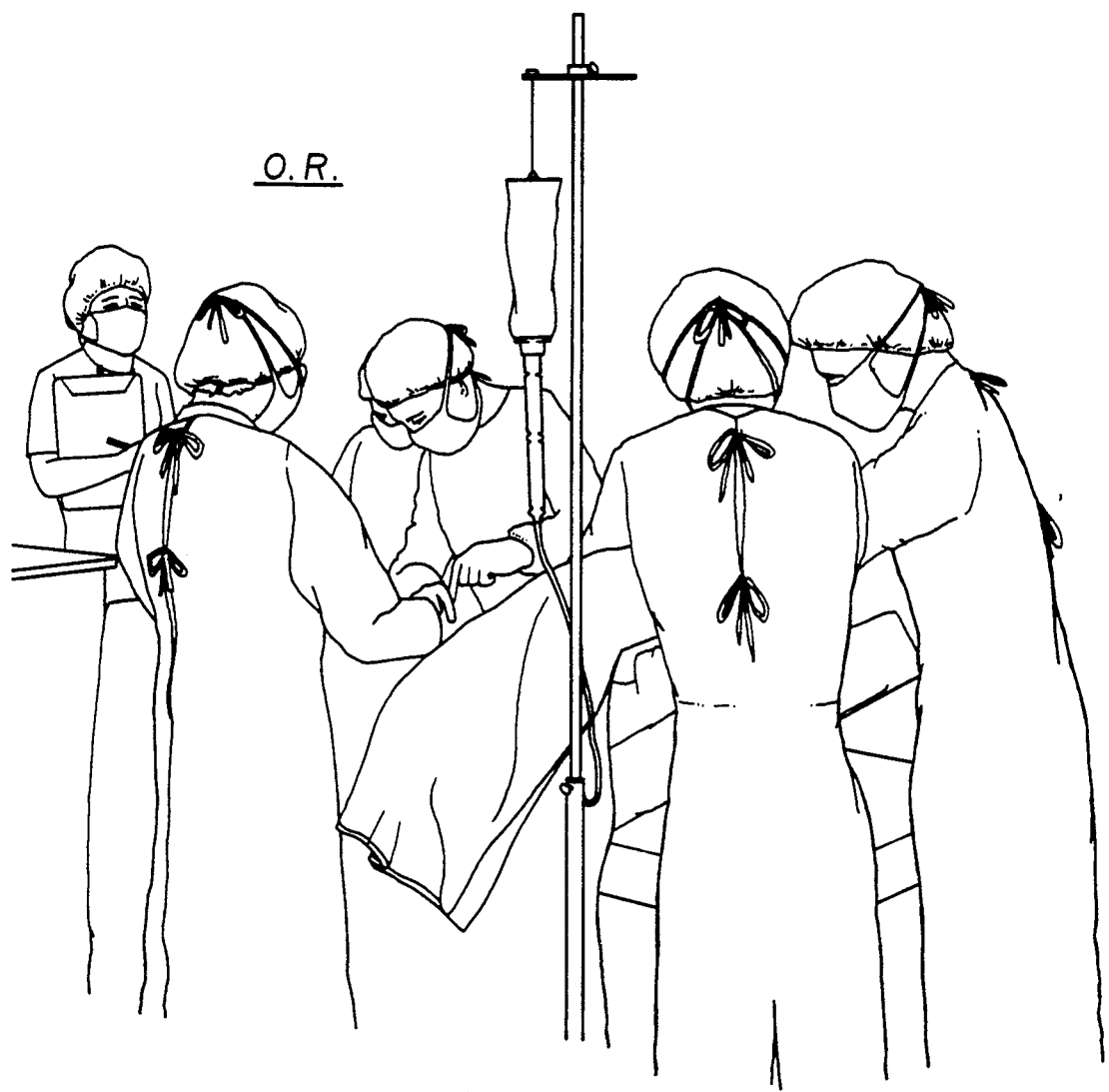
FIG. 1 is a perspective view of an operating theater where the guarded skin hook of the present invention will be utilized.

Referring to the drawings, the guarded skin hook 10 of the present invention includes a surgical skin hook 11 that is disposed within a protective guard 12. The hook 11 and the guard 12 may be selectively movable relative to one another, so that the prongs 14 of the hook 11 may be selectively positioned so as to be either retracted into, or extended from, the protective guard 12. The skin hook 11 and protective guard 12 of the guarded skin hook 10 of the present invention are designed so as to be readily adaptable for use in a surgical procedure, such as those which are carried out in standard operating theaters (FIG. 1).

Figure 2A:
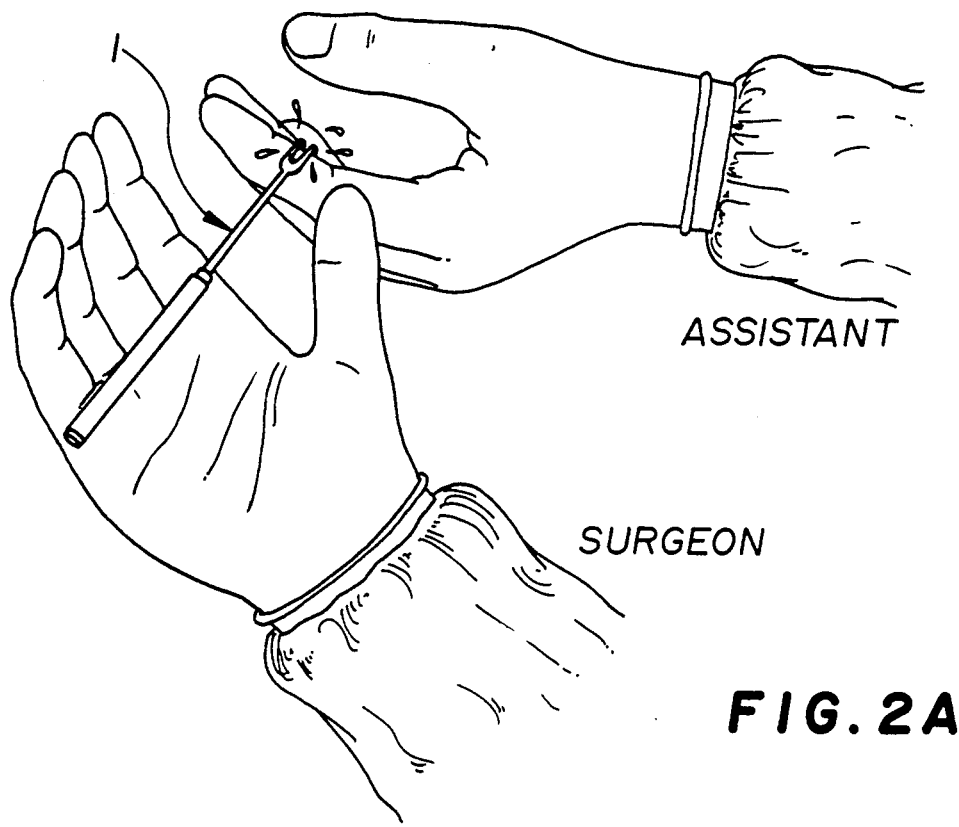
FIG. 2A is an enlarged view of a conventional skin hook, illustrating the problems that can occur to an assistant when passing a conventional skin hook to a surgeon during an operation.
Figure 2B:
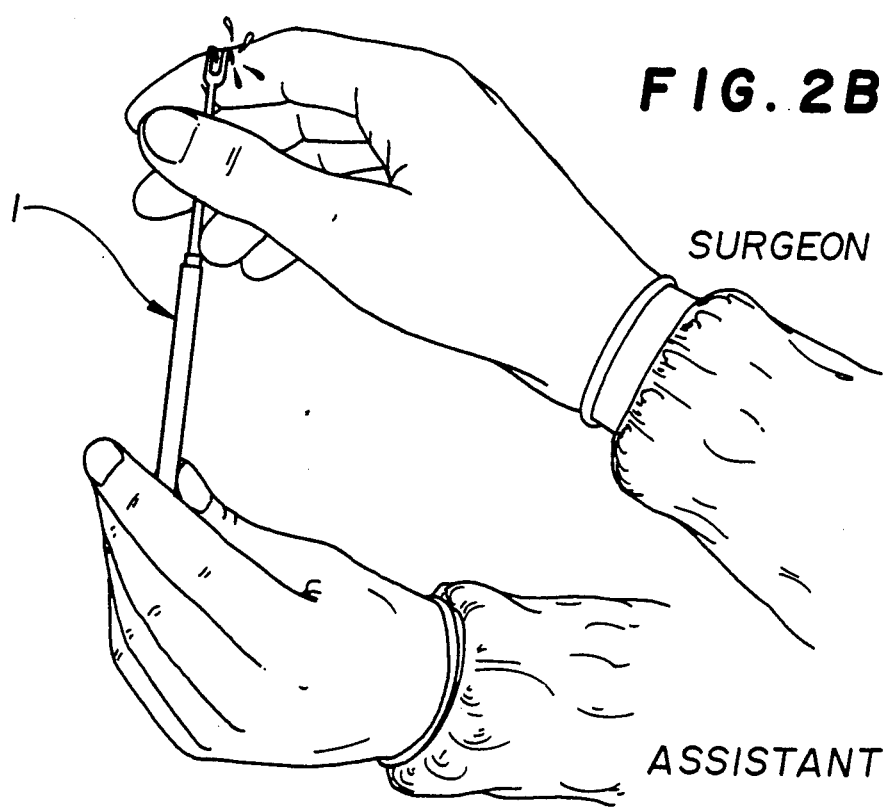
FIG. 2B is an enlarged view of a conventional skin hook, illustrating the problems that can occur to a surgeon when passing a conventional skin hook to the assistant during an operation.

As was discussed above, relative to FIGS. 2A and 2B, when conventional unguarded skin hooks 1 are passed between a doctor and an assistant during a surgical procedure, either one or the other of them are often stuck by the uncovered, exposed surgical prongs of the skin hook 1. It will be appreciated, of course, that "puncture" includes nicks, scrapes, cuts or the like.

The guarded skin hook 10 of the present invention remedies the long-standing problem (of operating room personnel being punctured, nicked or cut) by providing a skin hook 11 that is equipped with the protective guard 12.

This guard 12 receives therein the skin hook 11, including the main body thereof, for selective limited longitudinal movement of the skin hook 11 relative the guard 12, with the use of one hand and without the necessity of the surgeon having to remove his or her eyes away from the patient. Such movement is between a first, extended position and a second, retracted position.

With specific reference to FIGS. 3 and 7, in the first extended position, the surgical prongs 14 of the skin hook 10 of the present invention extend outwardly from the protective guard sleeve 12. In this position, the surgical prongs 14 of the skin hook 11 are substantially exposed (or uncovered) for permitting the normal usage thereof.

With reference to FIGS. 6 and 8, in the second retracted position, the surgical prongs 14 of the skin hook 10 of the present invention are retracted within the protective guard sleeve 12. In this manner, the guard 12 extends about the surgical prongs 14 of the skin hook 11, so that the prongs 14 are substantially covered by the guard sleeve 12. In this position, when not in usage, protection is afforded against accidental contact with the prongs 14 of the skin hook 11, so that the guarded skin hook 10 may be safely passed between an assistant and a surgeon, and vice versa, without inadvertently or accidentally sticking or cutting either the assistant or the surgeon.

To retain the prongs 14 in the position selected, the skin hook 10 includes a resiliently-biased detent means 13, which is formed between the skin hook 11 and the protective guard 12 of the guarded skin hook 10 of the present invention.

The resiliently-biased detent means 13 of the skin hook 10 of the present invention automatically locks the skin hook 11 and the protective guard 12 in place in the selected extended and retracted positions, respectively. In this fashion, the positioning of the guard 12 may be made by the health care provider using only one hand without the necessity of having to remove his or her eyes away from the patient. The detent means 13 also provides a release means which may be easily located or identified with a tactile means and utilized during a surgical operation for releasing the skin hook 11 and the protective guard 12, so that these elements 11 and 12 may be moved forwardly and rearwardly relative to one another and into the respective extended and retracted positions thereof. Finally, this same detent means 13 provides the skin hook 10 with an auditory sound means that provides a signal to the user when the skin hook 11 and the protective guard 12 have been locked into the selected extended and retracted positions thereof.

With further reference to FIGS. 3–13, the particular features and advantages of the guarded skin hook 10 of the present invention will be more readily appreciated.

Advantageously, the users of the guarded skin hook 10 may use the resiliently-biased detent means 13 (as shown more clearly in FIGS. 7 and 8) to release the skin hook 11 and the protective guard 12. In this manner, the skin hook 11 may be easily and selectively slidably moved relative to the protective guard 12 (which is held in the user's hand) forwardly into the first, extended position and rearwardly into the second, retracted position. More importantly, the resiliently-biased detent means 13 permits the user to selectively extend and retract the skin hook 11 with the use of only one hand and without the necessity of having to remove his or her eyes away from the patient in order to visually observe the guarded skin hook 10.

The skin hook 11 of the present invention includes a rearward main body portion 15. In conventional skin hooks, such a main body portion 15 is used as the handle which is gripped during use of the skin hook. However, and with particular reference to FIGS. 7 and 8, the main body portion 15 of the skin hook 11 of the guarded skin hook 10 of the present invention is "cut-off" or otherwise reduced in longitudinal length (by, for example, one-half of its regular length of, for example, three inches). Such a feature permits the overall longitudinal length of the guarded skin hook 10 (which includes the hook 11, as well as the guard 12) of the present invention to approximate the longitudinal length of conventional unguarded skin hooks, which are usually either six or eight inches in length. In this fashion, the guarded skin hook 10 of the present invention gives the particular health care provider, such as a surgeon, the same "feel" when using the guarded skin hook 10 as when using a conventional unguarded (and somewhat dangerous) skin hook.

The main body 15 of the skin hook 11 is elongated in shape, with a forward portion (or section) terminating in a forward end 15a and a rearward portion (or section) terminating in a rearward end 15b.

Extending forwardly and outwardly from the forward end 15a of the main body 15 is the skin hook portion 16. The surgical prongs 14 are formed on the (forward) end of this hook portion 16. Normally, the prongs 14 are about ⅛ inch apart. Conventionally, two such prongs 14 are formed. However, it should be noted that as few as one prong 14 may be provided. Conversely, as many as three or four such prongs 14 may be provided, as desired.

The protective guard 12 of the present invention is also seen to be elongated in shape. In this respect, the guard 12 is in the form of a sleeve, with a forward portion terminating in an open forward end (see FIG. 4) and a rearward portion terminating in a rearward end that is closed by a rearward wall 12a (as shown in FIG. 5). The guard sleeve 12 is slidably disposed over the body 15. In this fashion, the guard sleeve 12 is carried on the main body 15 of the skin hook 11 with the longitudinal axis of the guard 12 being substantially aligned with the longitudinal axis of the skin hook 11.

The shape of the exterior surface of the protective guard 12 generally approximates or mirrors the shape of the external surfaces of the handles of conventional skin hooks. Such a shape facilitates the use of the guarded skin hook 10 of the present invention by providing the user with a "feel" that is substantially the same as the "feel" provided by conventional skin hooks. In this manner, the user may grip the guarded skin hook 10 in the same manner as gripping a conventional skin hook.

Preferably, the guarded skin hook 10 of the present invention is formed with an exterior surface which is hexagonal in cross-section (FIGS. 9–12). In this fashion, an improved grip of the guarded skin hook 10 is provided while maintaining the familiar "feel" as conventional unguarded skin hooks. Further, such a hexagonal shape prevents undesired "rolling" of the device 10 on, for example, a table or similar flat surface, when the skin hook is not in use.

With reference to FIG. 12, preferably the interior surface of the protective guard 12 and the main body 15 of the skin hook 11 are both shaped so as to be substantially hexagonal in lateral cross-section. Such an arrangement insures that the skin hook 11 and the guard 12 are "keyed" to one another so as to prevent undesired relative rotation of the skin hook 11 within the guard 12.

Figure 13:
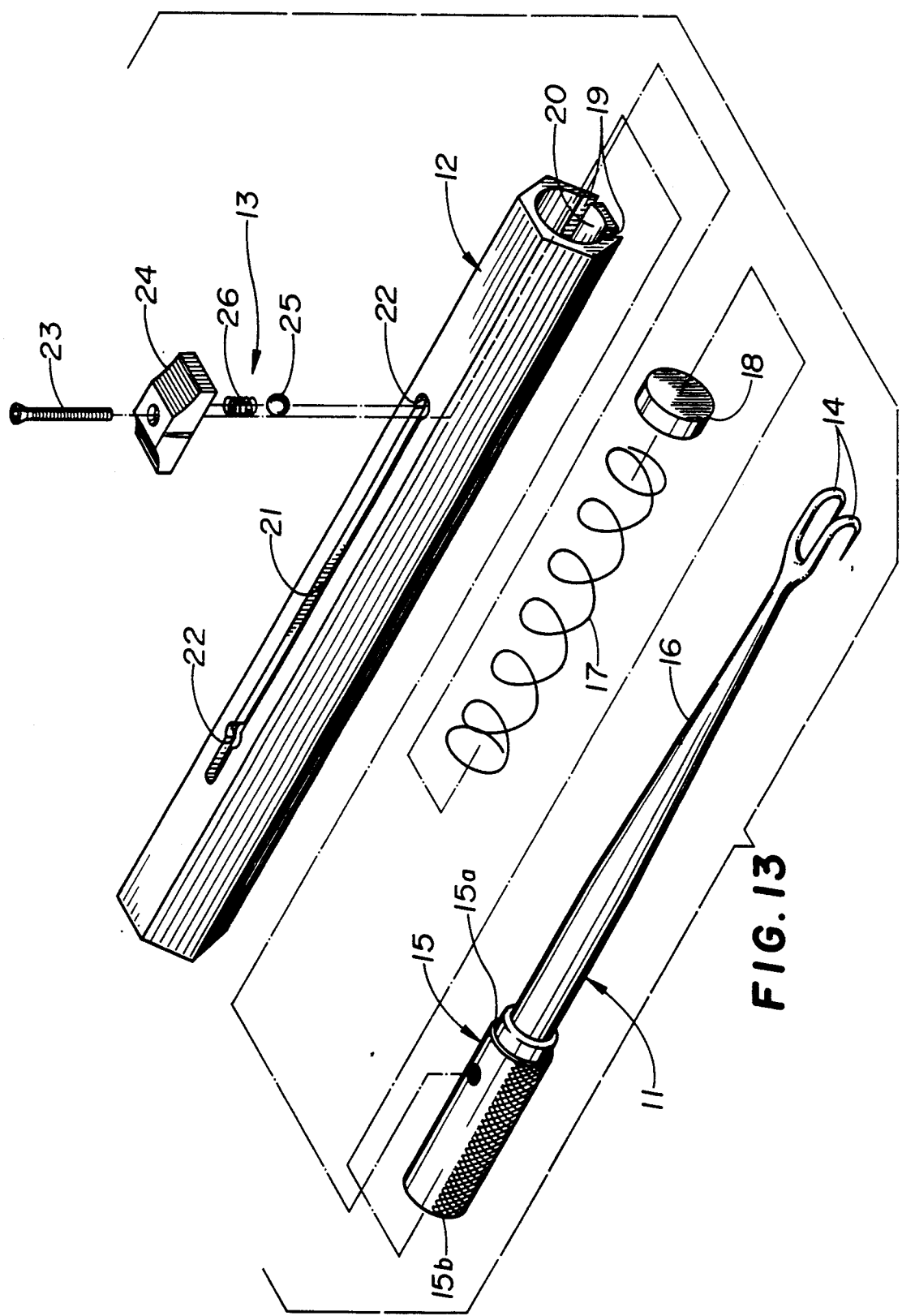
FIG. 13 is an exploded perspective view of the guarded skin hook of the present invention.

With particular reference to FIGS. 7 and 8, as well as to FIG. 13, a resilient biasing spring 17 is disposed in the guard sleeve 12, and is positioned between the rearward end of the main body 15 of the skin hook 11 and the rearward end of the sleeve 12. Preferably, a foot plate 18 is provided in the guard sleeve 12 and is positioned between the main body 15 and the closed end of the guard sleeve 12. Thus, the skin hook 11 is constantly resiliently-biased outwardly and into the extended position thereof. The spring 17 is a fairly "light" spring, so that when the button 24 is pushed forwardly, the detent ball 25 is released from the pocket 22 in the slot 21. In this fashion, the hook 11 will not spring outwardly like a javelin or a switchblade knife, but will still provide the resilient-biasing action. This is because the thumb has more strength in adduction than abduction and makes sense ergonomically.

With particular reference to FIGS. 5 and 13, the forward end of the guard sleeve 12 has a respective prong slot 19 formed therein for each prong 14 on the skin hook 11. In this embodiment two prong slots 19 are provided and are separated by a respective flange 20.

When the skin hook 11 is slid into its retracted position, the prongs 14 are received within their respective slots 19. The closeness of the flange 20 to the prongs 14 aids in preventing inadvertent contact with the surgical prongs 14 from occurring. In this fashion, surgeons, nurses and the like are guarded against inadvertent contact with the prongs 14, thereby preventing cuts or nicks normally encountered in usage and passing of the skin hook 11 between surgeons, nurses and the like during operating procedures. Accordingly, the risk of surgeons, nurses and the like inadvertently acquiring an infectious disease, such as HIV or HBV, in operating rooms or similar environments is substantially reduced.

Having thus described the skin hook 11 and the protective guard 12 of the preferred embodiment of the guarded skin hook 10 of the present invention, and with particular reference now to FIGS. 7-10 and 13, the resiliently-biased detent means 13 (the releasable detent locking means and the detent releasing means) will now be discussed.

To provide the selective longitudinal sliding movement of the skin hook 11 within its protective guard 12, the guard 12 has a closed slot 21 formed therein. This slot 21 extends longitudinally between the forward end and the rearward end of the guard 12. The limits of this closed slot 21 define the respective extended and retracted positions of the skin hook 11. The ends of the closed slot 21 are formed slightly larger than the remainder of the slot 21, thereby providing respective detent seats or pockets 22.

A transverse stem 23 having a first end and a second opposite end is provided. The first end of the stem 23 is integral with the main body 15 of the skin hook 11 internally of the guard sleeve 12, so as to project outwardly therefrom, transversely thereof (see FIG. 10). In this manner, the stem 23 extends through the slot 21, so that the forward and rearward movement of the stem 23 within the slot 21 (and hence the skin hook 11) defines the respective extended and retracted positions of the skin hook 11.

Figure 10:
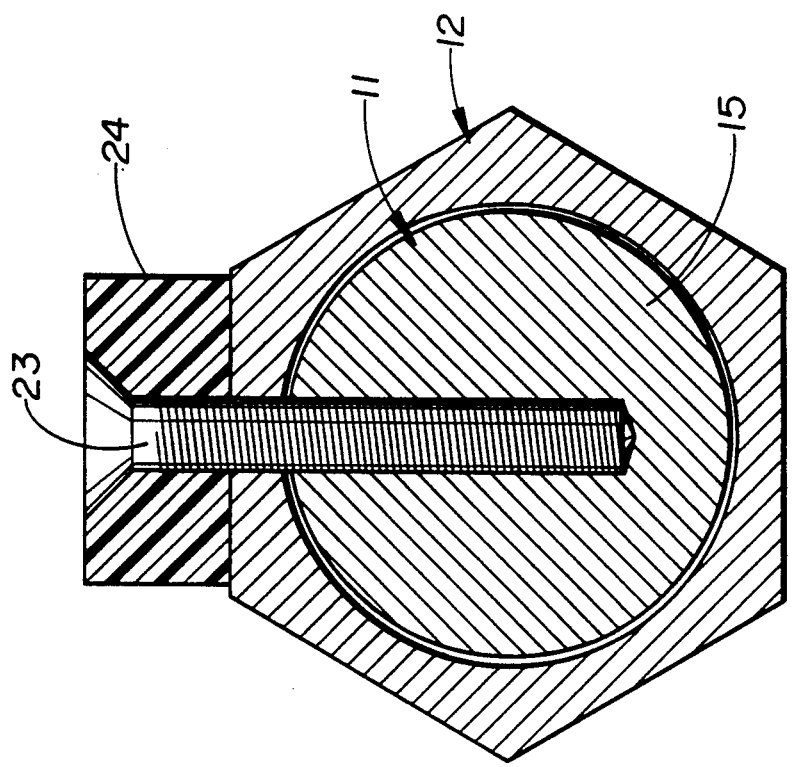
FIG. 10 is a cross-sectional view taken along lines 10—10 of FIG. 8.
Figure 9:
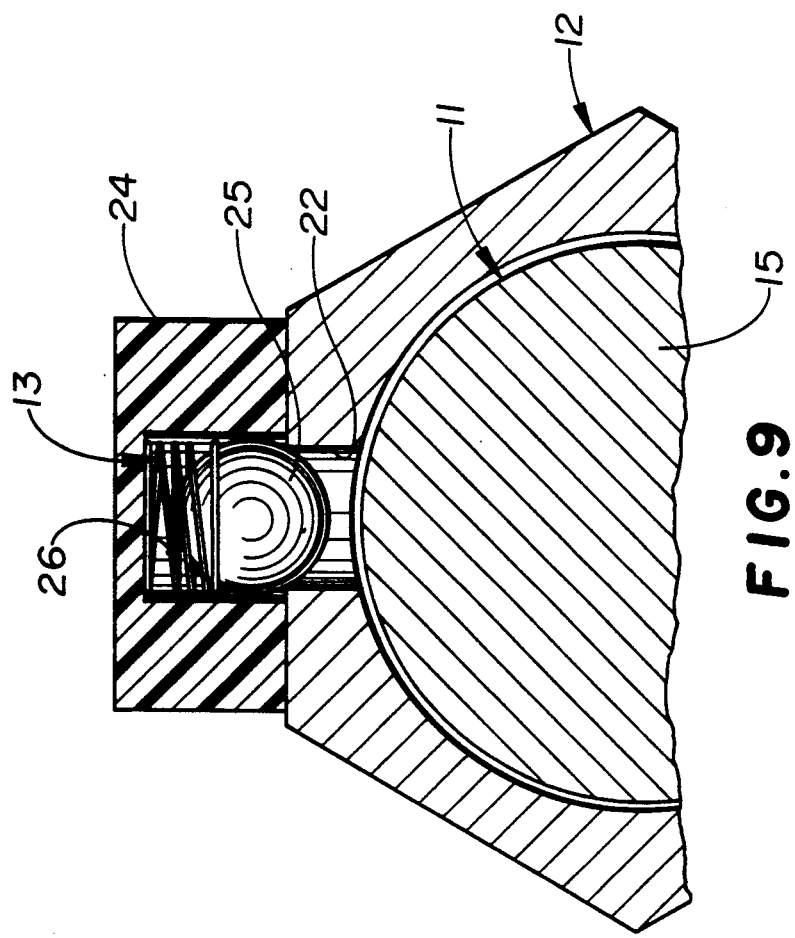
FIG. 9 is a cross-sectional view taken along lines 9—9 of FIG. 8.

The second end of the stem 23 is integral with a slide button 24 that, in turn, is disposed exteriorly of the guard sleeve 12 (see FIG. 10). In this fashion, the slide button 24 is held in place on the exterior surface of the guard sleeve 12. Preferably, the stem 23 is in the form of a recessed Allen-head screw that does not extend above the contours of the slide button 24.

A resiliently-biased detent ball 25 is carried by the slide button 24 for sliding movement therewith between the respective extended and retracted positions. The detent ball 25 is constantly resiliently-biased by a spring 26 towards the guard sleeve 12. However, it is to be expressly understood that another equivalent resiliently-biased element could be substituted therefor.

When the skin hook 11 is in its respective extended and retracted positions, the detent ball 25 is spring-biased into the respective detent pockets 22 for releasably retaining the skin hook 11 in its respective selected position. The detent ball 25 may be selectively cleared from the detent seats 22 simply by further manual movement of the slide button 24 that overcomes the biasing action of the spring 26, so as to allow the skin hook 11 to be slidably manually moved between the respective extended and retracted positions thereof.

Referring now to FIGS. 15-18, the operation of the above-described first embodiment of the guarded skin hook 10 of the present invention, and its features and advantages, will be more readily appreciated.

Figure 15:
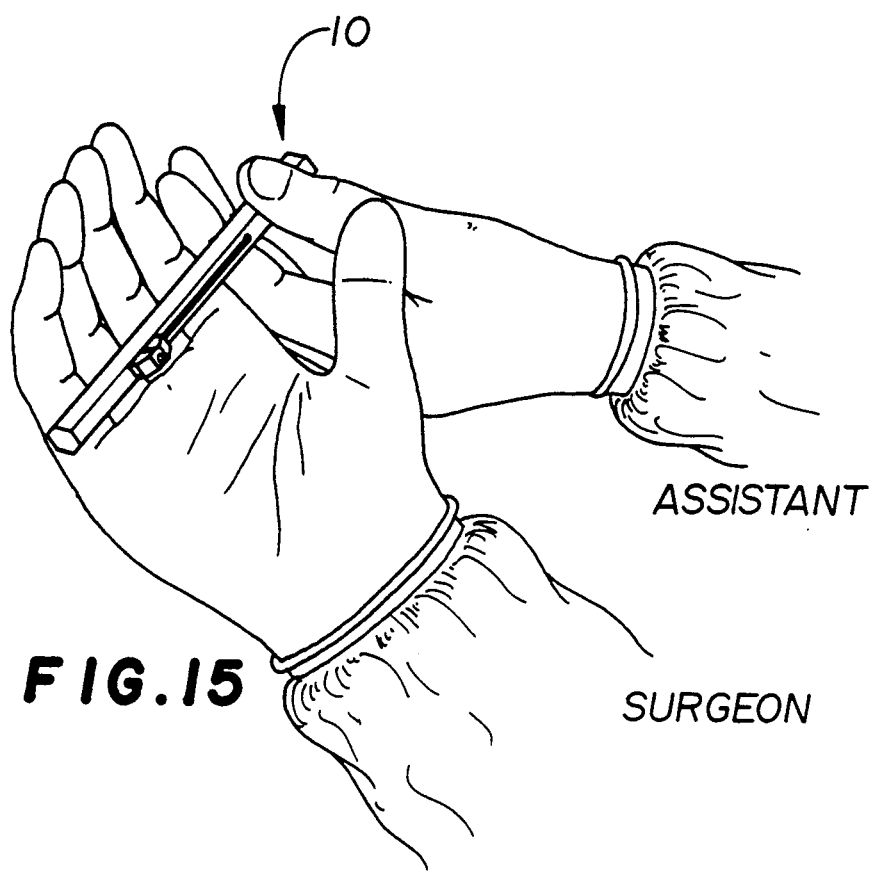
Figure 16:
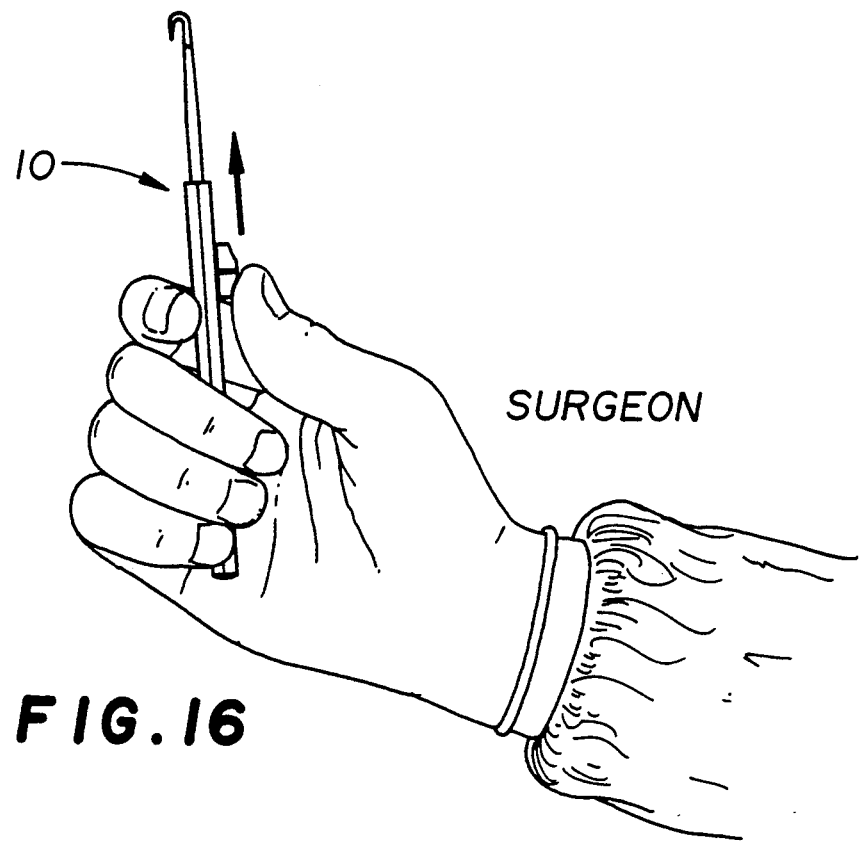

With the guarded skin hook 10 positioned in the retracted position thereof, a nurse or assistant may freely pass the guarded skin hook 10 of the present invention to a surgeon or other health care provider with a "slap" in his or her hand, so that the surgeon can feel the guard skin hook 10 including the orientation thereof (FIG. 15). With the guard skin hook 10 in the retracted position thereof, the surgeon has no need to remove his or her eyes from the patient to take the guard skin hook 10. With the skin hook 11 in its retracted position, wherein the prongs 14 of the skin hook 11 are shielded (or covered) by the protective guard 12, there is little or no danger of either the surgeon or the nurse or other assistant being nicked or cut thereby.

Once the surgeon has been given the guard skin hook 10, he or she may easily locate the release mechanism thereof (the slide button 24) which may be easily tactily located by its extension outwardly from the sleeve 12. Once the release mechanism is located, the doctor may the move the skin hook 11 into the extended position thereof merely by pushing the slide button 24 forwardly (FIG. 16) without taking or removing his or her eyes from the patient. Such pressure on the button 24 overcomes the biasing action of the spring 26, thereby unseating the ball detent 25 from the respective detent seat 22. In this manner, the skin hook 11 is unlocked and released for manual movement forwardly in the direction of the arrow and into the extended position thereof. Once in the extended position, the detent ball 25 is once again seated in a detent seat 22 (automatically, by the spring 26) where the ball 25 is locked and held in place during use of the skin hook 10. It is noted that the force of the spring 26 pushing the ball 25 into the seat 22 creates an auditory sound (namely, a "click") that notifies the user thereof that the skin hook 10 is locked into the desired position thereof.

Once the surgeon has finished with the guarded skin hook 10, he or she needs merely to slidingly move the skin hook 11 again, this time rearwardly and into the retracted position thereof, merely by pushing the slide button 24 rearwardly (FIG. 17) without taking or removing his or her eyes from the patient. Such pressure on the button 24 once again overcomes the biasing action of the spring 26, thereby unseating the ball detent 25 from the respective detent seat 22. In this manner, the skin hook 11 is unlocked and released for manual movement rearwardly in the direction of the arrow and into the retracted position thereof. Once in the retracted position, the detent ball 25 is again seated in its respective detent seat 22 by the spring 26 with a "click", whereby it is locked and held in place during use thereof.

With the guarded skin hook 10 now once again positioned in the retracted position thereof, the doctor may freely pass the guarded skin hook 10 of the present invention to a nurse or other assistant without removing his or her eyes from the patient and without any regard whatsoever for the orientation thereof (FIG. 18). With the skin hook 11 in its retracted position wherein the prongs 14 of the skin hook 11 are shielded (or covered) by the protective guard 12, there is little or no danger of either the doctor or the nurse or other assistant being nicked or cut thereby.

It is noted that, in order to achieve the above-mentioned goals of permitting safe handling of the guard skin hook 10 and the one-handed retraction and extension, without the necessity of visual observation, the resiliently-biased detent means 13 that is formed between the body 15 of the skin hook 11 and the protective guard 12, provides the following features and advantages:

(1) a locking means that is formed between the skin hook 11 and the protective guard 12 which selectively locks the skin hook 11 and the guard 12 relative to one another in the retracted and extended positions thereof, so that the guard 12 and the skin hook 11 will not be accidently dislodged or moved as a result of ordinary pressure being exerted thereon by the user while gripping the skin hook 10 during the use thereof;

(2) a release means formed between the skin hook 11 and the protective guard 12 that may be tactily and readily identified and utilized (operated) by a use with only one hand, and without the necessity of the user having to visually observe the guard skin hook 10, for selectively unlocking the skin hook 11 and the guard 12 relative to one another, so that the skin hook 11 and the guard 12 are released relative to one another for the longitudinal sliding movement between the retracted (rearward) and the extended (forward) positions thereof; and (3) an auditory warning means formed between the skin hook 11 and the protective guard 12 that provides an auditory signal or sound (a click) when the guard 12 and the skin hook 11 have been locked relative to one another in the selected (extended or retracted) position thereof, whereby the user may be made aware that the skin hook 11 and the protective guard 12 have actually been locked relative to one another in the selected (retracted or extended) position without the necessity of the user having to visually observe the skin hook 10.

Figure 14:
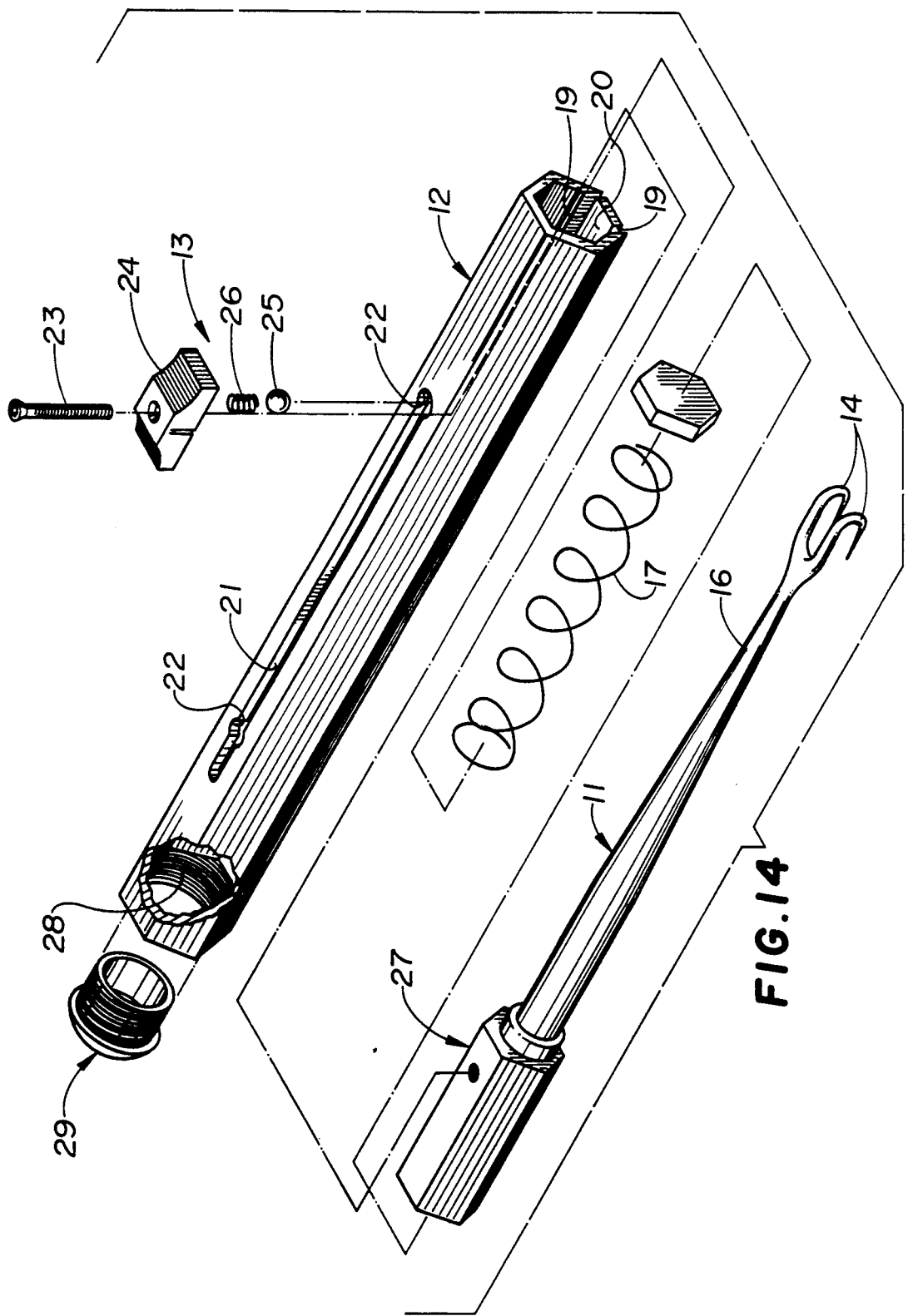
FIG. 14 is another exploded view, corresponding substantially to that of FIG. 13, but showing an alternate construction of the guarded skin hook of the present invention.

With reference of FIGS. 12 and 14, an alternate embodiment of the guarded skin hook 10 of the present invention is illustrated. There the main body portion 27 is hexagonally shaped so as to be complementary to the hexagonal shape of the guard sleeve 12, thereby keying the body 27 to the sleeve 12 and preventing relative rotation therebetween. Additionally, the sleeve 12 is completely tubular (open at both ends) and its rearward portion is internally threaded (as at 28) to receive an externally-threaded cap 29. This construction simplifies the assembly of the guarded skin hook. Its operation, however, and its features and advantages are identical to the embodiment of FIGS. 3-11 and 13.

The guarded skin hooks of the present invention accomplish these objectives consonant with economy of manufacture, convenient replacement of parts, and serviceability during life of the product.

Obviously, many modifications may be made without departing from the basic spirit of the present invention. For example, the respective inner and outer configurations of the protective guard sleeve may be round, hexagonal or any desired shape. Accordingly, it will be appreciated by those skilled in the art that within the scope of the appended claims, the invention may be practiced other than has been specifically described herein.

What is claimed is:

1. A guarded skin hook for surgical use comprising a skin hook having a main body and a forward section having a pair of spaced-apart parallel prongs formed thereon, a guard sleeve slidably receiving therein the skin hook including the main body thereof, means for slidably mounting the skin hook within the guard sleeve for limited longitudinal movement of the skin hook between a first extended position wherein the skin hook is extended from the guard sleeve so as to be exposed for usage and a second retracted position wherein the skin hook is retracted inside the guard sleeve so as to be covered by the guard sleeve for affording protection against accidental contact with the skin hook when not in usage, and wherein the guard sleeve has a pair of spaced-apart parallel slots formed therein to receive the respective prongs on the skin hook in the retracted position thereof.

2. The guarded skin hook of claim 1, further including a transverse stem integral with the main body of the skin hook and projecting outwardly from the main body transversely thereof, and the guard sleeve having a closed slot formed therein such that the stem extends therethrough, whereby the respective extended and retracted positions of the skin hook are defined by the limits of the closed slot.

3. The guarded skin hook of claim 2, wherein the guard sleeve has an exterior being shaped so as to be hexagonal in lateral cross-section, whereby an improved grip of the skin hook is provided.

4. The guarded skin hook of claim 1, further including a releasable detent locking means formed between the guard sleeve and the main body of the skin hook, the releasable detent locking means being operative in the respective extended and retracted positions of the skin hook, such that the skin hook may be selectively detent locked in the respective extended and retracted positions thereof.

5. The guarded skin hook of claim 4, wherein the releasable detent locking means includes a spring-loaded detent ball carried by the main body of the skin hook and the guard sleeve having a pair of detent pockets formed therein to selectively receive the detent ball when the skin hook is in the respective extended and retracted positions thereof, the detent ball being spring-loaded, such that when the skin hook is in the respective extended and retracted positions thereof the detent ball is spring-biased into the respective detent pockets for removably detent locking the skin hook in the respective selected position, and further such that the detent ball may be manually cleared from the respective detent pockets, so as to allow the skin hook to be slidably moved between the respective extended and retracted positions thereof.

6. The guarded skin hook of claim 4, wherein the releasable detent locking means includes a transverse stem having a first end being integral with the main body of the skin hook internally of the guard sleeve and projecting outwardly from the main body transversely thereof, the transverse stem further having a second opposite end, the guard sleeve having a closed slot formed therein, such that the stem extends therethrough, the closed slot having a pair of spaced detent seats formed therein, whereby the respective extended and retracted positions of the skin hook are defined by the positioning of the detent seats, and a slide button disposed exteriorly of the guard sleeve, the slide button being integral with the second end of the transverse stem externally of the main body, a detent stop carried by the slide button for sliding movement therewith between the respective extended and retracted positions the detent stop being spring-loaded, such that when the skin hook is in the respective extended and retracted positions thereof the detent stop is spring-biased into the respective detent seats for removably detent locking the skin hook in the respective selected position, and the detent stop further being resiliently-biased, such that the detent stop may be selectively cleared from the respective detent seats by manual movement of the slide button, so as to allow the skin hook to be slidably moved between the respective extended and retracted positions thereof.

7. The guarded skin hook of claim 6, wherein the detent stop is a detent ball.

8. The guarded skin hook of claim 1, further including a resilient biasing spring disposed in the guard sleeve so as to be between the sleeve and the skin hook, such that the skin hook is constantly resiliently-biased outwardly and into the extended position thereof.

9. The guarded skin hook of claim 8, further including a foot plate disposed in the guard sleeve so as to be positioned between the main body of the skin hook and the guard sleeve, and further wherein the resilient biasing spring is disposed between the foot plate and the guard sleeve, such that the skin hook is constantly resiliently-biased outwardly and into the extended position thereof.

10. The guarded skin hook of claim 1, wherein the guard sleeve has an interior being shaped so as to be hexagonal in lateral cross-section, and further wherein the main body of the skin hook has an exterior being shaped so as to be hexagonal in cross-section, such that the main body of the skin hook and the guard sleeve are keyed to one another, whereby when the main body of the skin hook is disposed in the guard sleeve undesired rotation of the skin hook in the guard sleeve is prevented.

11. A guarded skin hook for surgical use comprising a skin hook having a main body and a forward section from which the skin hook extends, a guard sleeve slidably receiving therein the skin hook including the main body thereof, means for slidably mounting the skin hook within the guard sleeve for limited longitudinal movement of the skin hook between a first extended position wherein the skin hook is extended from the guard sleeve so as to be exposed for usage and a second retracted position wherein the skin hook is retracted inside the guard sleeve so as to be covered by the guard sleeve for affording protection against accidental contact with the skin hook when not in usage, wherein the skin hook has a two prongs formed thereon, and further wherein the guard sleeve has two prong slots formed therein, such that a flange is defined therebetween whereby when the skin hook is slid into the retracted position thereof the prongs of the skin hook are received in the respective prong slots.

12. A guarded skin hook for surgical use comprising a skin hook having a main body and a forward section having a pair of spaced-apart parallel prongs formed thereon, a guard sleeve slidably receiving therein the skin hook including the main body thereof, means for slidably mounting the skin hook within the guard sleeve for limited longitudinal movement of the skin hook relative to the guard sleeve between a first extended position wherein the skin hook is extended from the guard sleeve so as to be exposed for usage and a second retracted position wherein the skin hook is retracted inside the guard sleeve so as to be covered by the guard sleeve for affording protection against accidental contact with the skin hook when not in usage, a a releasable detent locking means for releasably detent locking the skin hook in the selected extended and retracted positions thereof, the releasable detent locking means including a transverse stem having a first end being integral with the main body of the skin hook internally of the guard sleeve and projecting outwardly from the main body transversely thereof, and the transverse stem further having a second opposite end, the guard sleeve having a closed slot formed therein for receiving the stem therethrough, the closed slot having a pair of spaced detent seats formed therein, thereby defining the respective extended and retracted positions of the skin hook, a slide button disposed externally of the guard sleeve, the slide button being integral with the second end of the transverse stem externally of the main body, a resiliently-biased releasable detent locking stop carried by the slide button for sliding movement therewith between the respective extended and retracted positions thereof, whereby the respective extended and retracted positions of the skin hook, the detent locking stop is operative by being removably biased into and received in the respective detent seat in the closed slot of the guard sleeve, thereby removably detent locking the skin hook in the respective selected extended and retracted positions thereof and wherein the guard sleeve has a pair of spaced-apart parallel slots formed therein to receive the respective prongs on the skin hook in the retracted position thereof.

13. The guarded skin hook of claim 12, wherein the detent locking stop is a detent ball.

14. The guarded skin hook of claim 12, further including a resilient biasing spring disposed in the guard sleeve so as to be between the sleeve and the skin hook, such that the skin hook is constantly resiliently-biased outwardly and into the extended position thereof.

15. The guarded skin hook of claim 14, further including a foot plate disposed in the guard sleeve, so as to be positioned between the main body of the skin hook and the guard sleeve, and further wherein the resilient biasing spring is disposed between the foot plate and the guard sleeve, such that the skin hook is constantly resiliently-biased outwardly and into the extended position thereof.

16. The guarded skin hook of claim 12, wherein the guard sleeve has an interior being shaped so as to be hexagonal in lateral cross-section, and further wherein the main body of the skin hook has an exterior being shaped so as to be hexagonal in cross-section, such that the main body of the skin hook and the guard sleeve are keyed to one another, whereby when the main body of the skin hook is disposed in the guard sleeve undesired rotation of the skin hook in the guard sleeve is prevented.

17. A guarded skin hook for surgical use comprising a skin hook having a main body and a forward section from which the skin hook extends, a guard sleeve slidably receiving therein the skin hook including the main body thereof, means for slidably mounting the skin hook within the guard sleeve for limited longitudinal movement of the skin hook relative to the guard sleeve between a first extended position wherein the skin hook is extended from the guard sleeve so as to be exposed for usage and a second retracted position wherein the skin hook is retracted inside the guard sleeve so as to be covered by the guard sleeve for affording protection against accidental contact with the skin hook when not in usage, a releasable detent locking means for releasably detent locking the skin hook in the selected extended and retracted positions thereof, the releasable detent locking means including a transverse stem having a first end being integral with the main body of the skin hook internally of the guard sleeve and projecting outwardly from the main body transversely thereof, and the transverse stem further having a second opposite end, the guard sleeve having a closed slot formed therein for receiving the stem therethrough, the closed slot having a pair of spaced detent seats formed therein, thereby defining the respective extended and retracted positions of the skin hook, a slide button disposed externally of the guard sleeve, the slide button being integral with the second end of the transverse stem externally of the main body, a spring-loaded releasable detent locking stop carried by the slide button for sliding movement therewith between the respective extended and retracted positions thereof, whereby in the respective extended and retracted positions of the skin hook, the detent locking stop is operative by being removably biased into and received in the respective detent seat in the closed slot of the guard sleeve thereby removably detent locking the skin hook in the respective selected extended and retracted positions thereof, wherein the skin hook has two prongs formed thereon, and further wherein the guard sleeve has two prong slots formed therein, such that a flange is defined therebetween, whereby when the skin hook is slid into the retracted position thereof, the prongs of the skin hook are received in the respective prong slots.

18. A guarded skin hook for surgical use comprising a skin hook having a main body and a forward section having a pair of spaced-apart parallel prongs formed thereon, a guard sleeve slidably receiving therein the skin hook including the main body thereof, means for slidably mounting the skin hook within the guard sleeve for limited longitudinal movement of the skin hook relative to the guard sleeve between a first extended position wherein the skin hook is extended from the guard sleeve so as to be exposed for usage and a second retracted position wherein the skin hook is retracted inside the guard sleeve so as to be covered by the guard sleeve for affording protection against accidental contact with the skin hook when not in usage, the means for slidably mounting the skin hook within the guard sleeve including a spring-loaded detent ball carried by the main body of the skin hook, the guard sleeve having a pair of detent pockets formed therein to selectively receive the detent ball, whereby the skin hook may be selectively detent locked in the respective extended and retracted positions thereof, and further whereby the detent ball may be manually cleared from the respective detent pockets, so as to allow the skin hook to be slidably moved between the respective extended and retracted positions thereof and wherein the guard sleeve has a pair of spaced-apart parallel slots formed therein to receive the respective prongs on the skin hook in the retracted position thereof.

19. A guarded skin hook for surgical use comprising a skin hook having a main body and a forward section having a pair of spaced-apart parallel prongs formed thereon, a guard sleeve slidably receiving therein the skin hook including the main body thereof, means for slidably mounting the skin hook within the guard sleeve for limited longitudinal movement of the skin hook between a first extended position wherein the skin hook is extended from the guard sleeve so as to be exposed for usage and a second retracted position wherein the skin hook is retracted inside the guard sleeve so as to be covered by the guard sleeve for affording protection against accidental contact with the skin hook when not in usage, the skin hook further including a releasable detent locking means for releasably locking the skin hook in the selected extended and retracted positions thereof and wherein the guard sleeve has a pair of spaced-apart parallel slots formed therein to receive the respective prongs on the skin hook in the retracted position thereof.

20. A guarded skin hook for use in surgical procedures, comprising a first member including a main body and further including a forwardly-extending tapered portion having a pair of spaced-apart prongs formed thereon, a second member telescopically receiving the first member, means for mounting the first and second members for limited relative longitudinal sliding movement therebetween, whereby the guarded skin hook has a first operational position in which the first member extends outwardly of the second member, such that the pair of spaced-apart prongs on the first member is exposed, and wherein the guarded skin hook further has a second guarded position in which the first member is retracted relative to the second member, such that the pair of spaced-apart prongs is substantially covered by the second member, two-position detent locking means between the first and second members, and a thumb-actuated slide button carried by one of the members for manually overcoming the detent locking means without requiring a lifting thereof away from the guard sleeve.

21. A guarded surgical skin hook, comprising a body, at least one prong, an intermediate tapered portion having a pair of ends, one end of which is connected to the prong and the other end of which is connected to the body, a guard sleeve telescopically receiving the body and having alternate advanced and retracted positions relative to the body, the guard sleeve having an elongated longitudinal slot formed therein, the slot having a pair of end portions providing detent pockets, a transverse stem carried by the body and having a portion projecting through the slot in the guard sleeve, a slide button mounted on projecting portion of the transverse stem, such that the slide button and the body slide in unison relative to the guard sleeve, the slide button having a blind transverse bore formed therein substantially parallel to the projecting portion of the transverse stem, a spring within the blind transverse bore, and a detent member carried by the slide button in the blind transverse bore therein, lodged between the spring and the guard sleeve, and received alternately in the respective detent pockets in the slot in the guard sleeve when the guard sleeve is moved alternately into its advanced and retracted positions.

22. A guarded skin hook for surgical use during an operating procedure, comprising a skin hook, said skin hook comprising a shank having a longitudinal axis and further having a forward portion provided with a plurality of prongs, the prongs being spaced apart, substantially parallel to each other, and disposed on respective opposite sides of the longitudinal axis of the shank, and a guard sleeve slidably mounted on the skin hook for relative limited movement thereon along the longitudinal axis, the guard sleeve having a retracted position in which the plurality of prongs are exposed and further having an advanced position in which the plurality of prongs are guarded, and two-position spring-loaded detent means between the guard sleeve and the skin hook and exerting a resilient bias transversely of the longitudinal axis, thereby facilitating a one-handed operation of the guard sleeve without looking at the skin hook during the operating procedure.

* * * * *